United States Patent [19]

Green et al.

[11] Patent Number: 4,566,620
[45] Date of Patent: Jan. 28, 1986

[54] ARTICULATED SURGICAL FASTENER APPLYING APPARATUS

[75] Inventors: David T. Green, Norwalk; Ernie Aranyi, Shelton, both of Conn.

[73] Assignee: United States Surgical Corporation, Norwalk, Conn.

[21] Appl. No.: 662,677

[22] Filed: Oct. 19, 1984

[51] Int. Cl.⁴ .......................... A61B 17/04; B25C 5/00
[52] U.S. Cl. ................... 227/19; 128/334 R; 227/DIG. 1
[58] Field of Search .................. 128/334 R, 334 C; 227/19, 20, DIG. 1

[56] References Cited

U.S. PATENT DOCUMENTS

| D. 274,096 | 5/1984 | Shutt | D24/27 |
| 4,204,623 | 5/1980 | Green | 227/19 |
| 4,473,077 | 9/1984 | Noiles et al. | 128/305 |
| 4,485,817 | 12/1984 | Swiggett | 128/334 R |
| 4,488,523 | 12/1984 | Shichman | 128/334 R |

FOREIGN PATENT DOCUMENTS 869527  3/1953  Fed. Rep. of Germany .

OTHER PUBLICATIONS

"Instructions for Use, Proximate ™ Flexible Linear Stapler", Ethicon, Inc., 1983.

*Primary Examiner*—Anton O. Oechsle
*Attorney, Agent, or Firm*—Robert R. Jackson; John E. Nathan

[57] ABSTRACT

In apparatus including a distal surgical fastener applying assembly operatively connected to a proximal actuator assembly by a longitudinal shaft assembly, the shaft assembly includes an articulation for allowing the fastener applying assembly to be placed in any of a wide range of rotational orientations relative to the actuator assembly.

32 Claims, 14 Drawing Figures

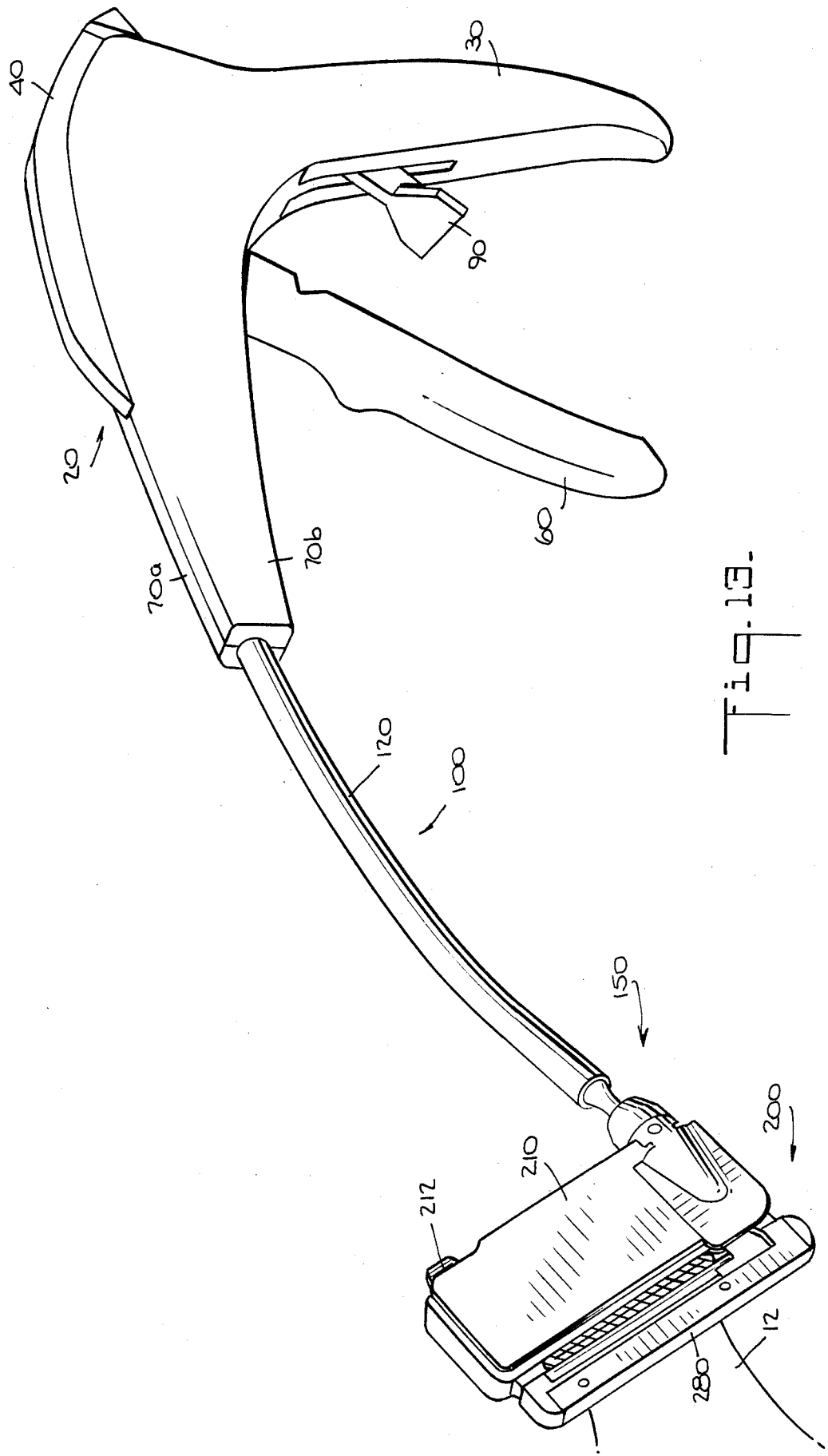

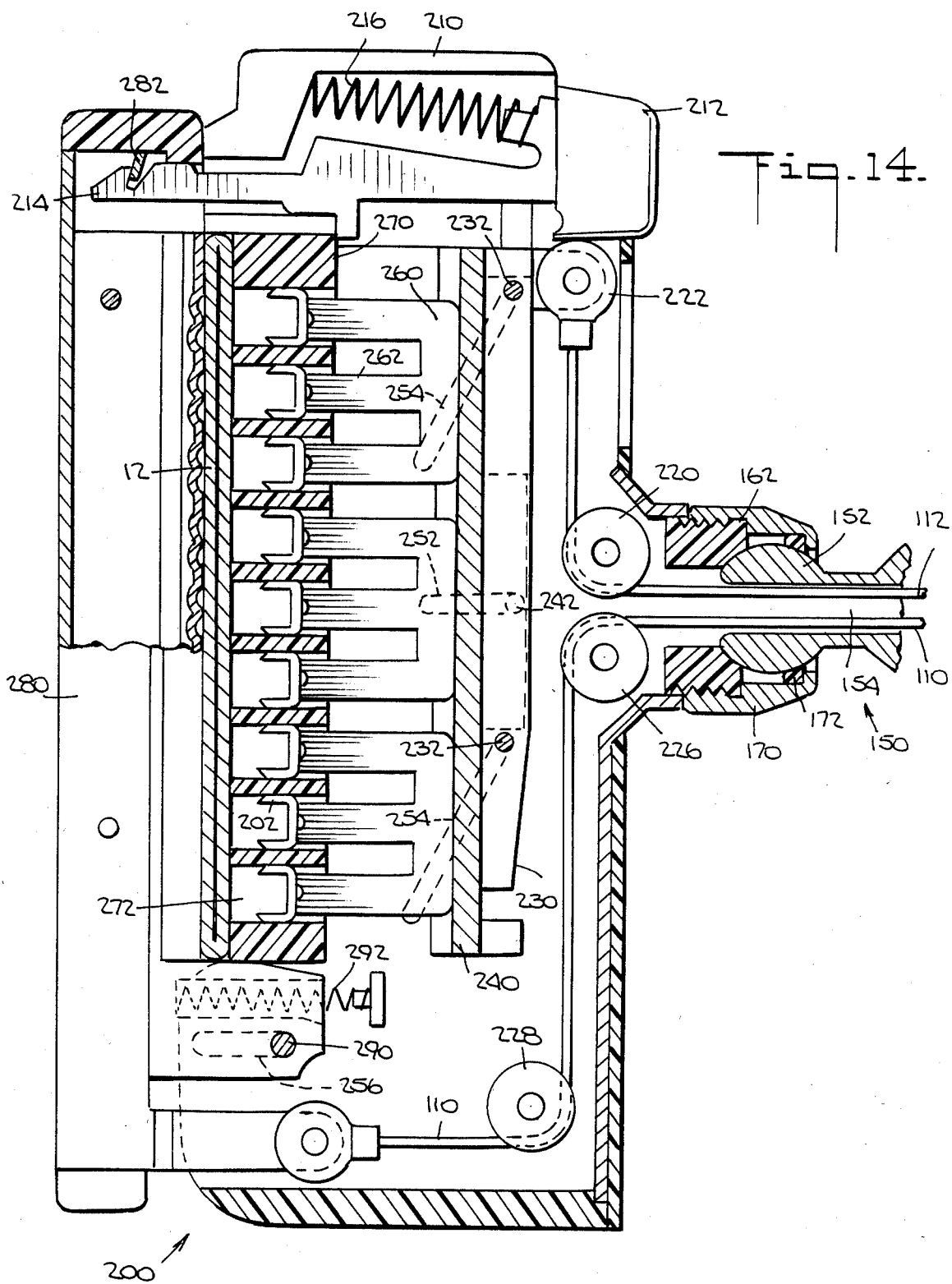

ARTICULATED SURGICAL FASTENER APPLYING APPARATUS

BACKGROUND OF THE INVENTION

This invention relates to surgical fastener applying apparatus, and more particularly to surgical fastener applying apparatus of the type which applies surgical fasteners to body tissue clamped between relatively movable fastener holding and anvil parts of the apparatus.

Several types of surgical fastener applying instruments are known for applying surgical fasteners to body tissue clamped between relatively movable fastener holding and anvil parts of the apparatus. See, for example, Hirsch et al. U.S. Pat. No. 3,275,211. The surgical fasteners may be either metal staples as shown in the Hirsch et al. patent, or they may be non-metallic resinous materials as shown, for example, in Green U.S. Pat. No. 4,402,445. In the case of metal staples, the staple legs are typically driven through the tissue and clinched by the anvil to secure the staples in the tissue. In the case of non-metallic fasteners, each fastener may initially consist of two separate parts: a fastener part disposed in the fastener holding part of the apparatus, and a retainer part disposed in the anvil part of the apparatus. The leg or legs of the fastener parts are driven through the tissue and interlock with the retainer parts to secure the fasteners in the tissue. Although most metal surgical staples are biologically inert and therefore remain permanently in the body, biologically absorbable metal surgical staples are known. Surgical fasteners of non-metallic resinous materials can also be made either biologically absorbable or non-absorbable.

The type or form of the fasteners employed forms no part of the present invention. The various types of fasteners are mentioned solely to establish that the term "surgical fastener" as used herein is generic to all of these types of fasteners, and to similarly establish that the terms "fastener holding part" and "anvil part" as used herein are also generic to instruments for applying all of these various types of fasteners.

In most of the known instruments for applying surgical fasteners to tissue clamped between the fastener holding and anvil parts of the instrument, the distal fastener applying assembly (which includes the fastener holding and anvil parts) of the instrument is rigidly connected to the proximal actuator portion of the instrument. This is true, for example, of the instruments shown in the above-mentioned Hirsch et al. and Green patents.

Recently, however, there has been increasing interest in instruments in which the connection between the fastener applying assembly and the actuator assembly is not completely rigid. For example, Noiles et al. U.S. Pat. No. 4,473,077 shows a surgical stapler in which the shaft assembly connected between the fastener applying and actuator assemblies is transversely flexible in one plane (i.e., the plane of the paper in Noiles et al. FIG. 5). This may be a desirable feature in an instrument of the type shown by Noiles et al. which is intended for insertion into a tubular body organ. In such applications the flexible shaft of the instrument conforms to the curvature of the surrounding body organ. However, in instruments which are not usually supported by surrounding body structures (e.g., instruments of the type shown in the above-mentioned Hirsch et al. and Green patents), excessive flexibility in the instrument between the fastener applying and actuator assemblies may mean that the position of the fastener applying assembly cannot be controlled from the actuator assembly and that each of these assemblies must be separately supported during placement of the instrument on the tissue to be fastened. This may mean that two people are required to handle the instrument during placement and removal.

In view of the foregoing, it is an object of this invention to provide surgical fastener applying apparatus of the type described above in which the fastener applying assembly is not rigidly connected to the actuator assembly but in which the location of the fastener applying assembly can be substantially controlled from the actuator assembly.

It is another object of this invention to improve and simplify surgical fastener applying apparatus of the type described above in which the fastener applying assembly is not rigidly connected to the actuator assembly.

SUMMARY OF THE INVENTION

These and other objects of the invention are accomplished in accordance with the principles of the invention by providing surgical fastener applying apparatus in which the fastener applying assembly is connected to the actuator assembly by a shaft assembly including an articulation or joint such as a ball rotatably mounted in a complementary socket. The joint preferably allows relative rotation of the fastener applying and actuator assemblies about each of three mutually orthogonal axes. Except for the joint, the shaft assembly is preferably transversely rigid. The joint can be made stiff enough so that although the aforementioned relative rotation is permitted, the fastener holding and actuator assemblies tend to retain their relative rotational orientations except when the configuration of the instrument is deliberately altered by the user. Thus, except for deliberate rotation of the fastener applying assembly, the entire apparatus can be positioned solely by manipulating the actuator assembly. It is not necessary to separately support the fastener applying assembly.

In the preferred embodiment the actuator assembly includes manually operable means for producing at least some of the work required for causing relative motion of the fastener holding and anvil parts to clamp the tissue to be fastened between those parts, and manually operable means for producing the work required for driving the fasteners through the clamped tissue. The work produced by these means is transmitted to the fastener applying assembly by proximal motion of transversely flexible members (e.g., cables) in the shaft assembly. These members preferably pass through the shaft assembly joint so that these members do not interfere with operation of the joint.

Also in the preferred embodiment, the fasteners are driven from the fastener holding part in the distal direction, and the fastener applying assembly includes means for converting the proximal motion of the shaft assembly member which transmits the work required for driving the fasteners to proportional distal motion of the fasteners.

Further features of the invention, its nature and various advantages will be more apparent from the accompanying drawings and the following detailed description of the invention.

BRIEF DESCRIPTION OF THE DRAWINGS

FIG. 13 is a perspective view of an alternative embodiment of the invention.

FIG. 14 is a view similar to FIG. 10 showing another alternative embodiment of the invention.

DETAILED DESCRIPTION OF THE INVENTION

Figure 1:
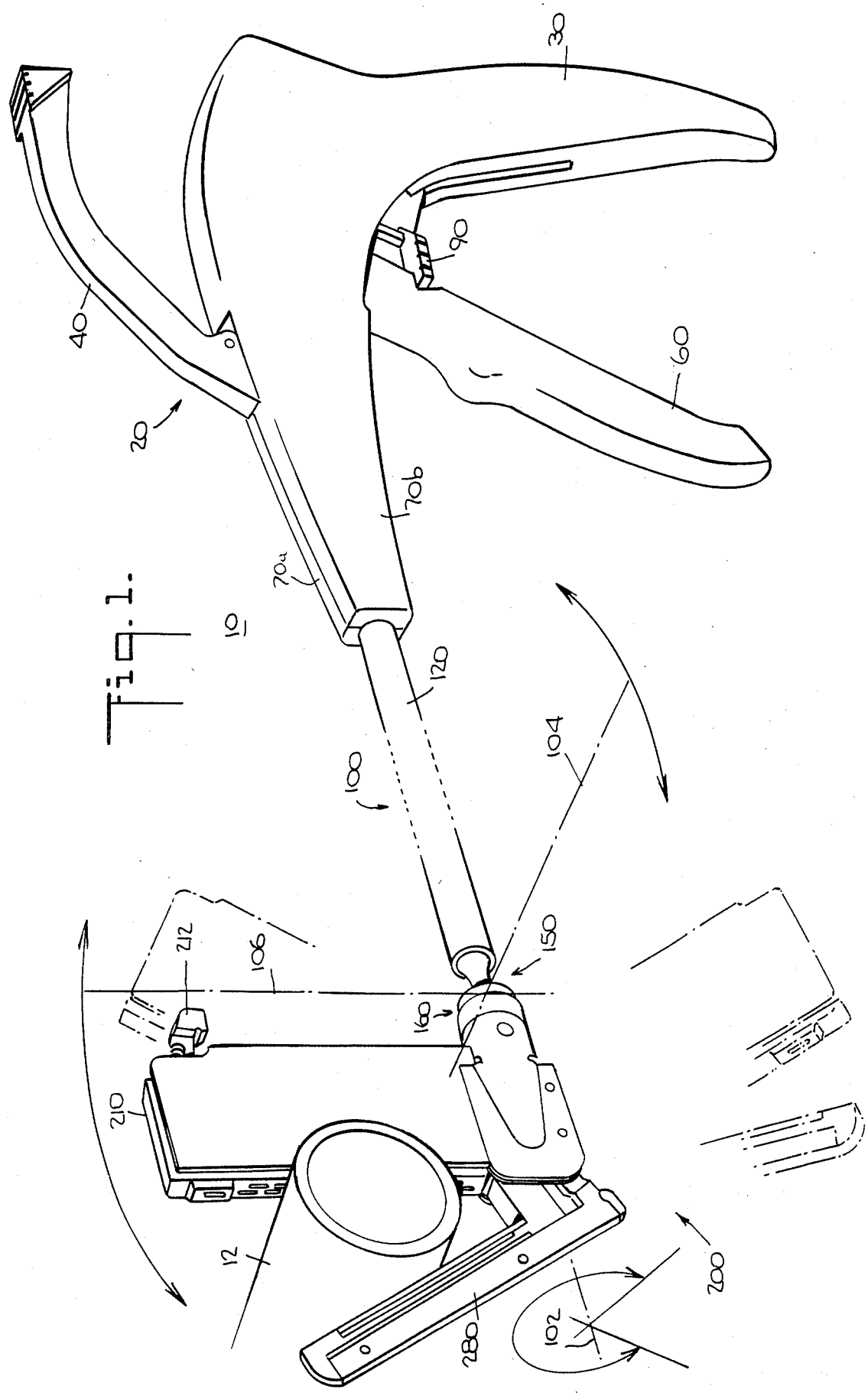
FIG. 1 is a perspective view of a first illustrative embodiment of the invention.

As shown in FIG. 1, an illustrative embodiment of the surgical fastener applying apparatus or instrument 10 of this invention includes proximal actuator assembly 20, distal fastener applying assembly 200, and intermediate shaft assembly 100.

Fastener applying assembly 200 includes proximal fastener holding part 210 and distal anvil part 280. Anvil part 280 is mounted for limited pivotal and translational motion relative to fastener holding part 210 so that anvil part 280 can be translated and pivoted away from fastener holding part 210 as shown in solid lines in FIG. 1 to permit the tissue 12 that is to be fastened to be inserted between the distal surface of fastener holding part 210 and the proximal surface of anvil part 280.

Fastener holding part 210 is connected to the distal end of shaft assembly 100 just beyond an articulation or joint 150 in the shaft assembly. In the illustrative embodiment, joint 150 comprises a spherical ball 152 (FIG. 2) rotatably secured in a complementary socket 160. Joint 150 allows fastener applying assembly 200 to rotate about each of three mutually orthogonal axes 102, 104, and 106, all of which intersect at the center of ball 152. A few of the possible positions of fastener applying assembly 200 are suggested in phantom lines in FIG. 1. The proximal end of shaft assembly 100 may also be rotatably mounted in actuator assembly 20 for additional rotational motion of assemblies 100 and 200 about axis 102, which is the longitudinal axis of the instrument. Other than joint 150 and the rotational mounting of shaft assembly 100 in actuator assembly 20, shaft assembly 100 is substantially rigid transverse to its longitudinal axis. Shaft assembly 100 is also substantially rigid parallel to axis 102.

Actuator assembly 20 includes proximal handle 30, manually operable clamp actuator lever 40, and manually operable fastener actuator lever 60. Pivoting clamp actuator lever 40 down into actuator assembly 20 pulls the lower portion of anvil part 280 toward fastener holding part 210. Squeezing fastener actuator lever 60 toward handle 30 causes fastener holding part 210 to drive the surgical fasteners contained in that part in the distal direction toward anvil part 280. Fastener actuator lever 60 cannot be operated until safety latch 90 is pivoted down away from lever 60 as shown in phantom lines in FIG. 3.

Figure 2:
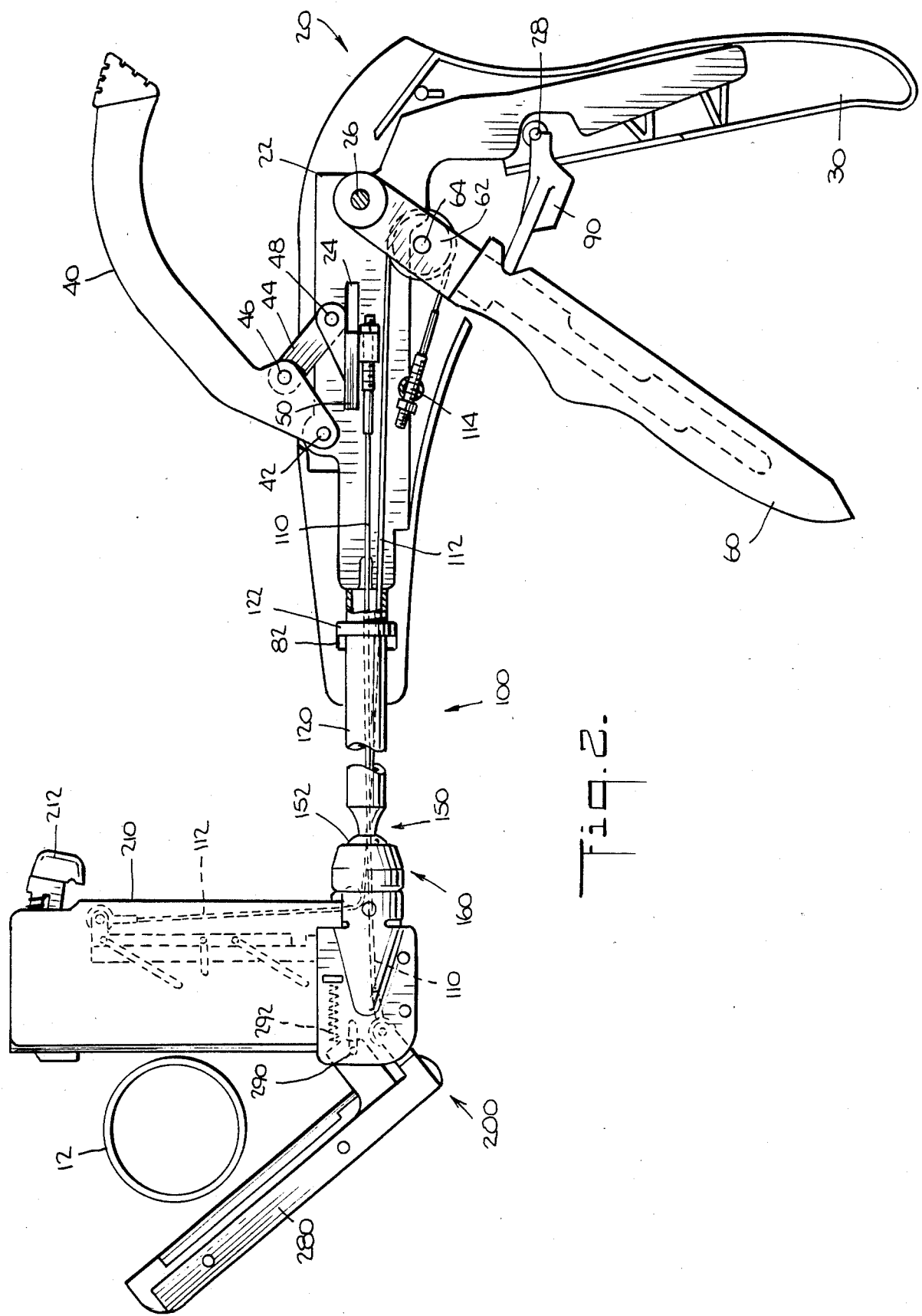
FIG. 2 is a partial, partly sectional, elevational view of the apparatus of FIG,. 1 showing an initial stage in the operating cycle of the apparatus.
Figure 8:
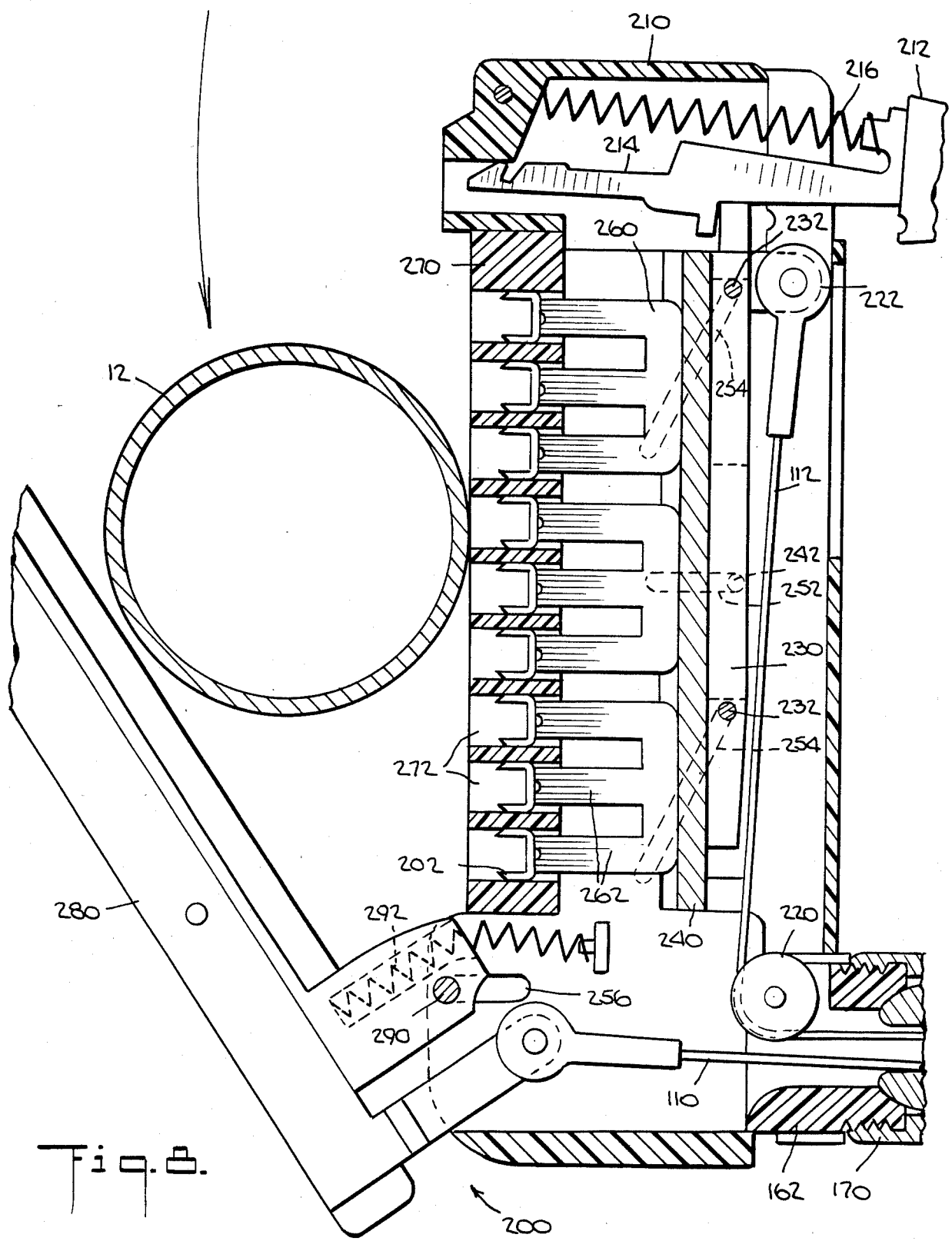
FIG. 8 is a partly sectional, elevational view of a portion of the apparatus of FIGS. 1-7 showing an initial stage in the operating cycle of that apparatus.

Before considering the construction of the apparatus in more detail, a brief description of its overall operation will be given. The initial condition of the apparatus is shown in FIGS. 1, 2, and 8. Fastener applying assembly 200 is rotated, if desired, by any desired amount about any of axes 102, 104, and 106 so that fastener applying assembly 200 has any desired angular orientation relative to actuator assembly 20. Joint 150 and the rotational connection between shaft assembly 100 and actuator assembly 20 are preferably tight enough so that during subsequent operation of the apparatus, assemblies 20 and 200 maintain whatever relative angular orientation they are placed in.

Figure 9:
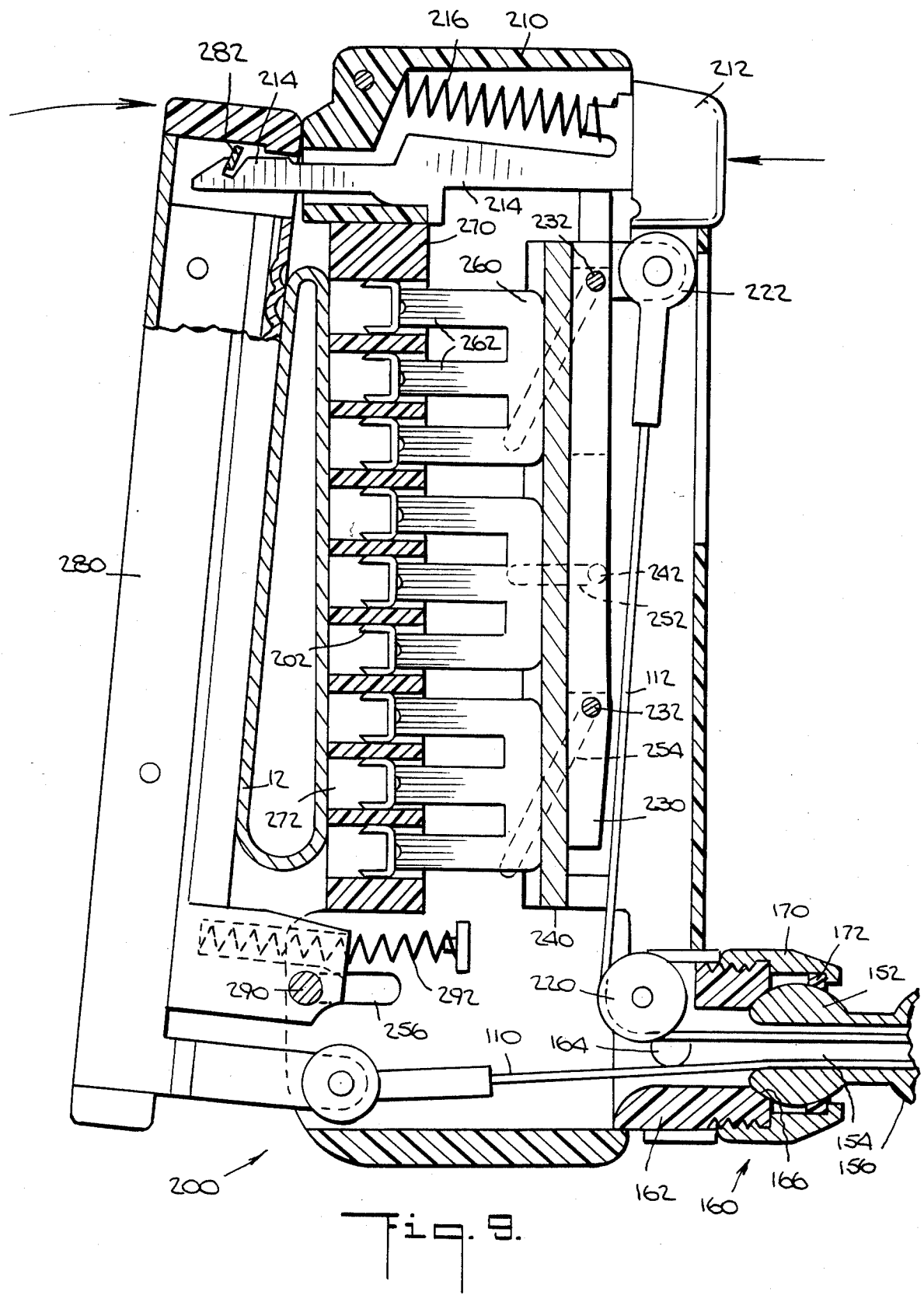
FIGS. 9-12 are views similar to FIG. 8 showing successive stages in the operating cycle of the apparatus.

The tissue 12 to be fastened is placed between anvil part 280 and fastener holding part 210. The upper portion of anvil part 280 is manually moved toward the opposite upper portion of fastener holding part 210 as shown in FIG. 9, and latch button 212 is manually pushed in the distal direction so that latch 214 engages catch 282 in anvil part 280. This holds the upper end of anvil part 280 against the upper end of fastener holding part 210 to begin the clamping of the tissue between those parts.

Figure 3:
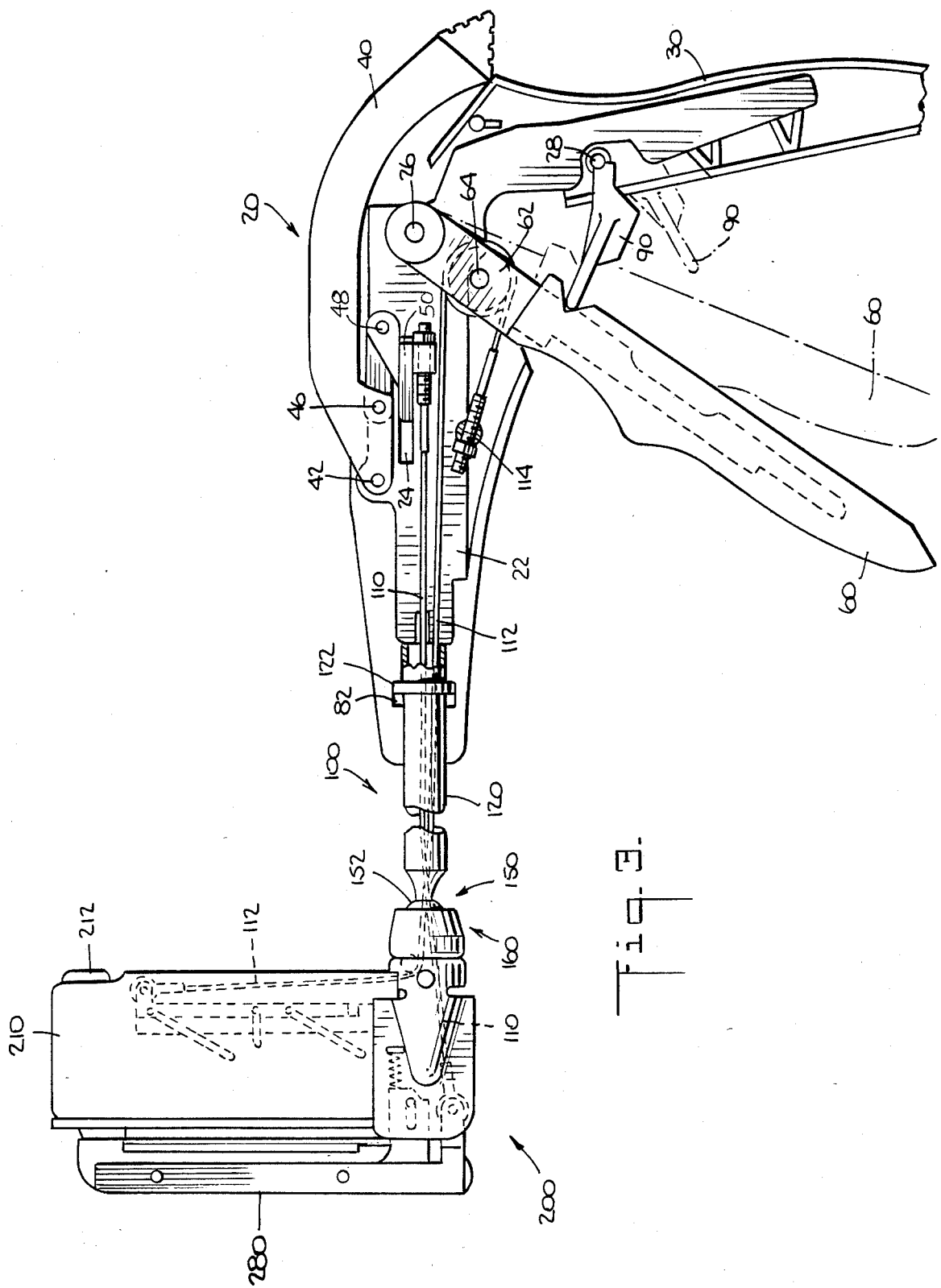
FIG. 3 is a view similar to FIG. 2 but showing a subsequent stage in the operating cycle.
Figure 10:
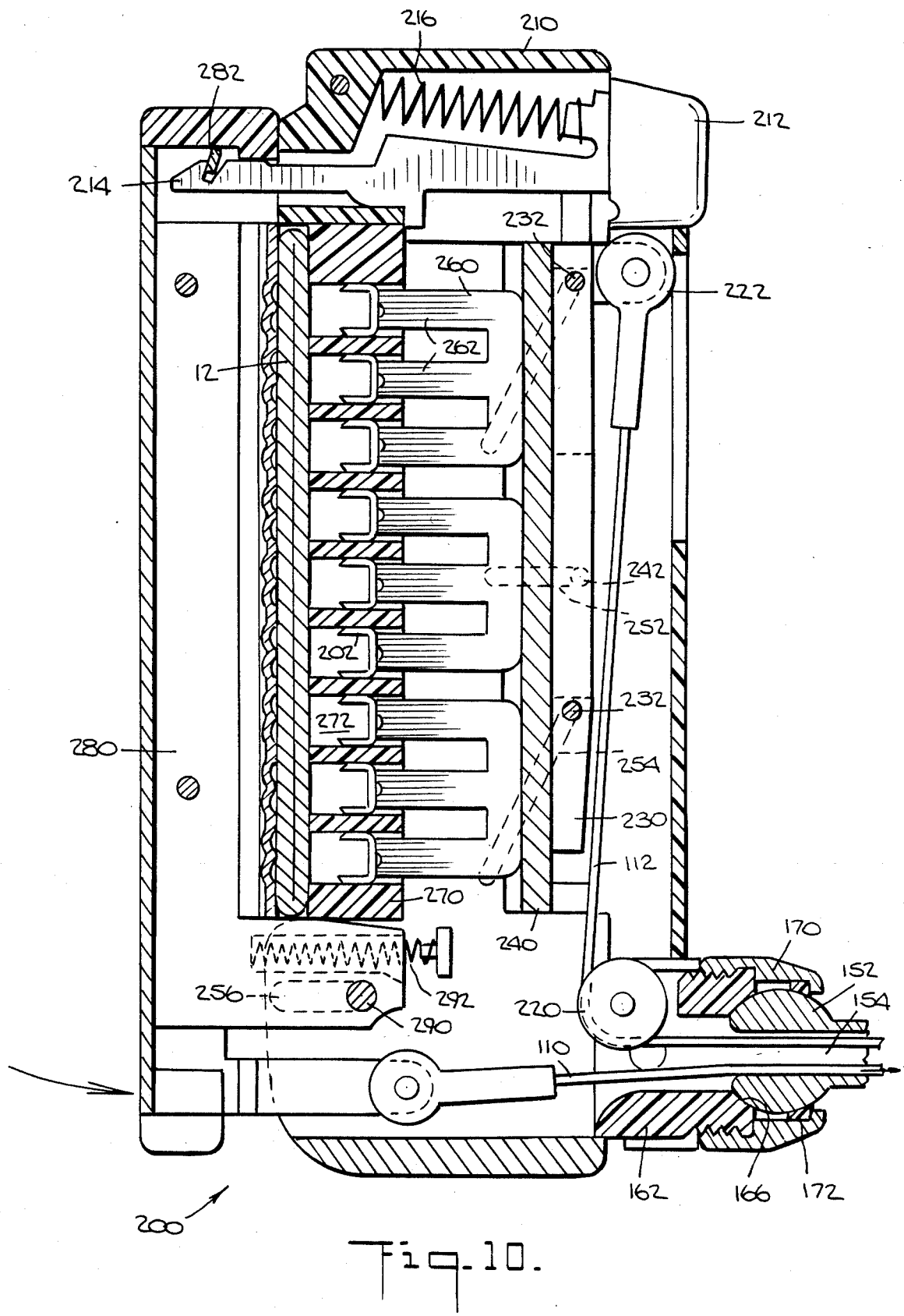

The next operating step is to pivot clamp actuator lever 40 down into actuator assembly 20 as shown in FIG. 3. This pulls the lower end of anvil part 280 in against the lower end of fastener holding assembly 210 as shown in FIGS. 3 and 10. Parts 210 and 280 are now substantially parallel to one another with tissue 12 firmly clamped between the opposing surfaces of those parts. The tissue is now ready to be fastened.

Figure 11:
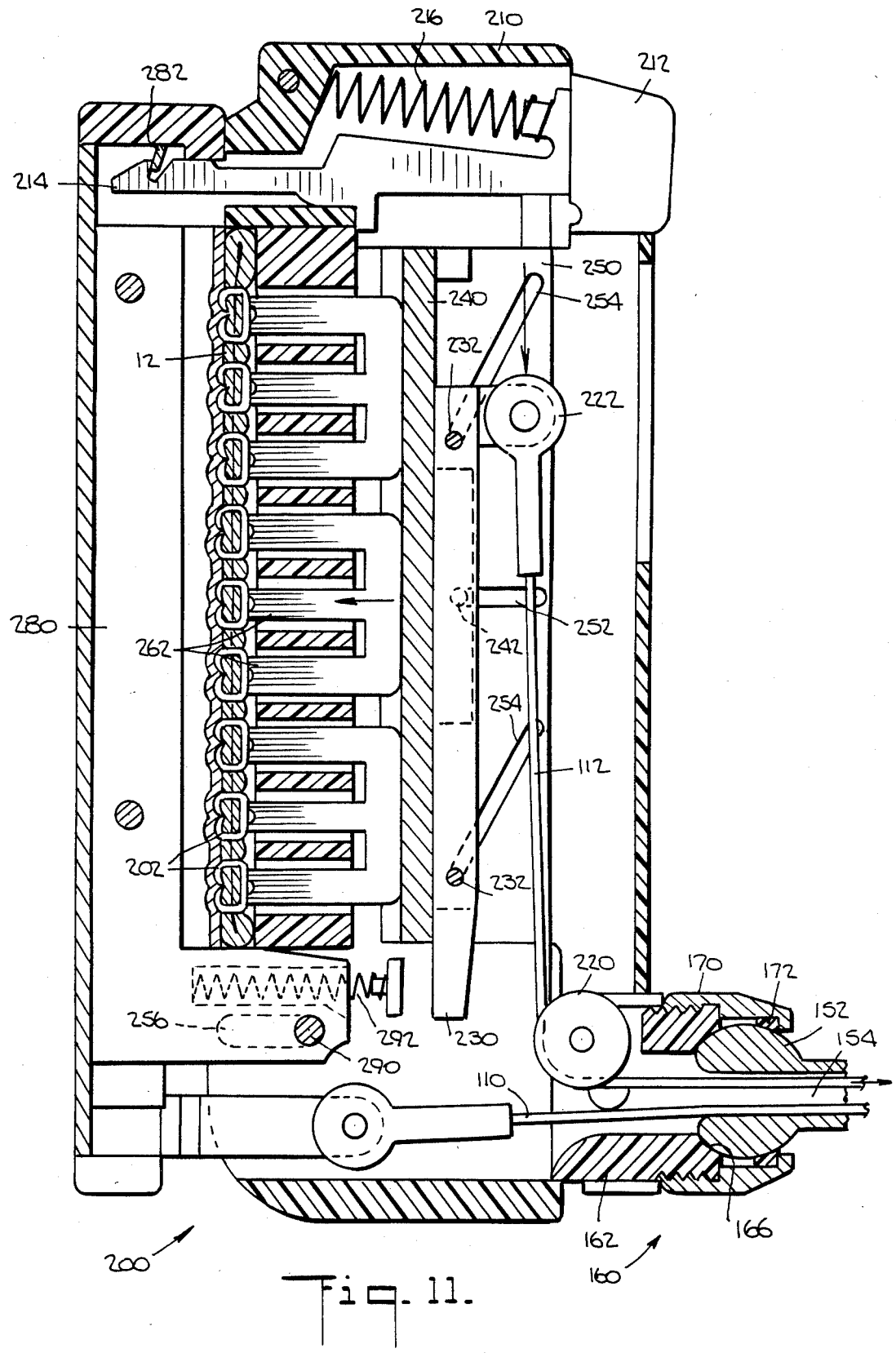

When the fasteners are to be applied, safety latch 90 is pivoted down as indicated in phantom lines in FIG. 3. Fastener actuator lever 60 is then pivoted toward handle 30 as also shown in phantom lines in FIG. 3. This causes fastener holding assembly 210 to simultaneously or substantially simultaneously drive the legs of a plurality of metal surgical staples 202 through tissue 12 and against anvil part 280 as shown in FIG. 11. Anvil part 280 clinches or crimps the ends of the staple legs to secure the staples in the tissue. (Although metal staples are employed in the depicted embodiment, it will be understood that two-part plastic fasteners, such as those shown in Green U.S. Pat. No. 4,402,445, can alternatively be used.) The tissue fastening procedure is now complete.

Figure 12:
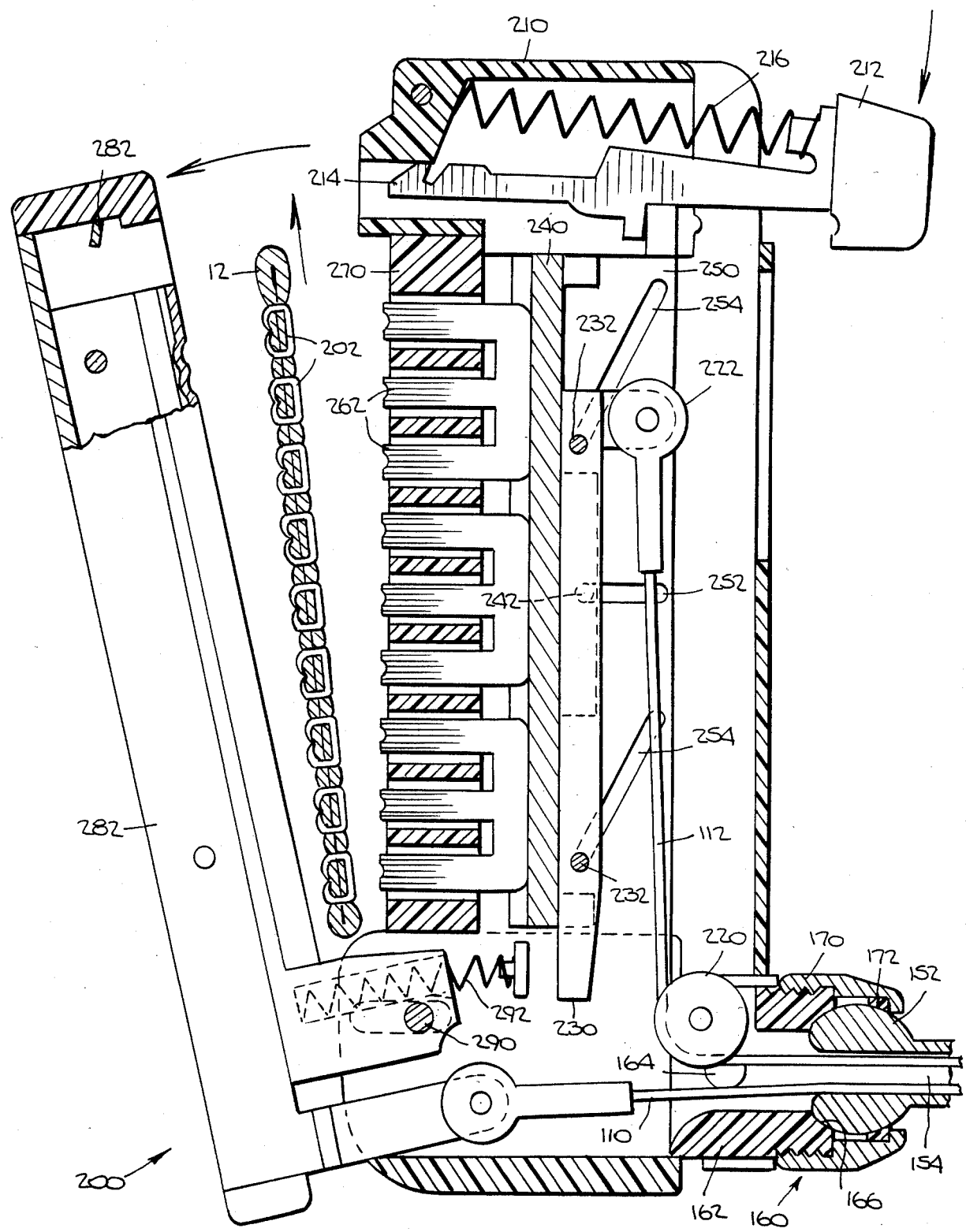

The fastened tissue is removed from the apparatus by manually pushing up on latch button 212 as shown in FIG. 12. This causes latch 214 to release catch 282, thereby allowing anvil part 280 to pivot away from fastener holding part 210. The fastened tissue can now be removed from the apparatus.

Figure 4:
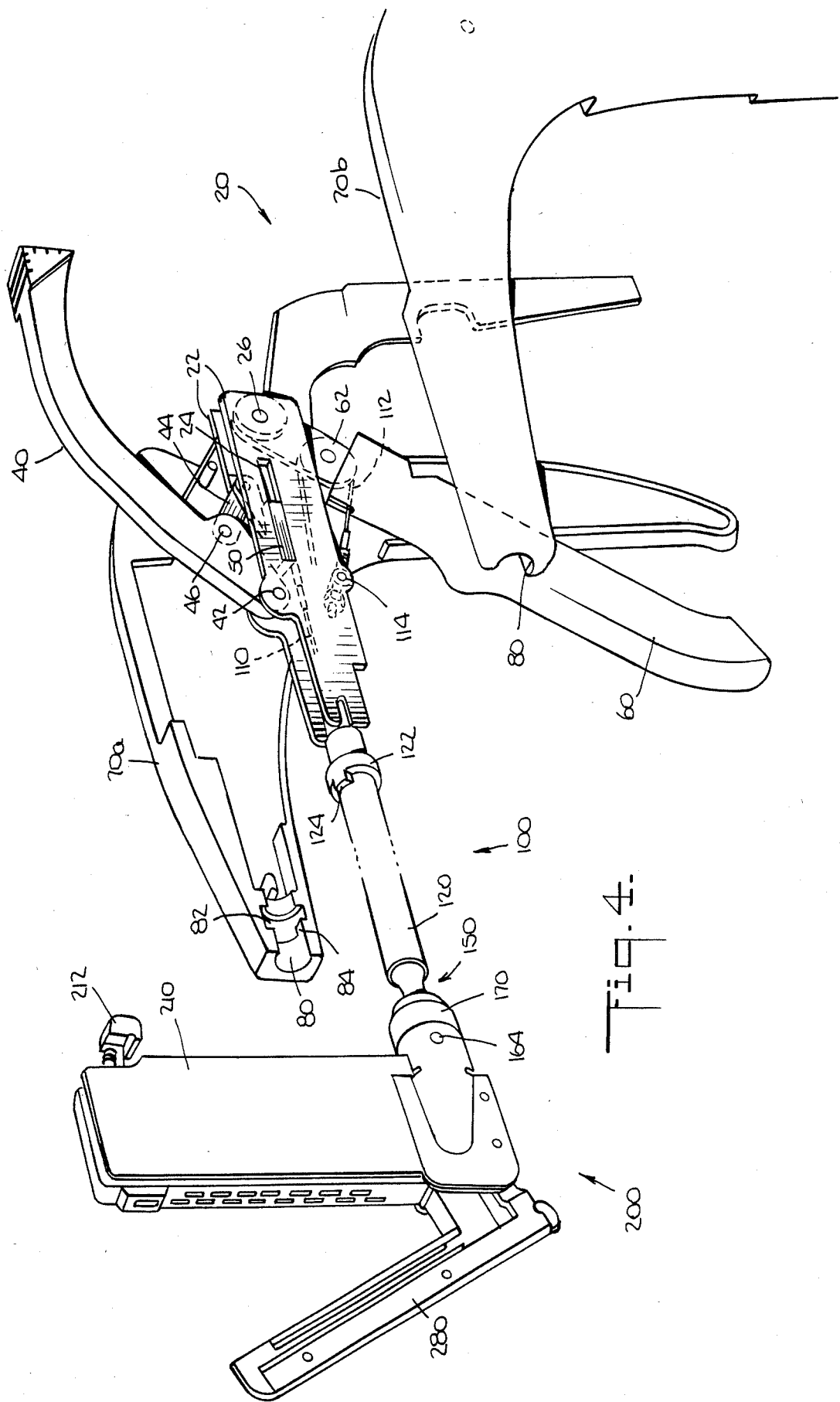
FIG. 4 is a partial exploded perspective view of the apparatus of FIGS. 1-3.

Considering now the internal construction and operation of the apparatus, first with reference to FIG. 2, clamp actuator lever 40 is pivotally connected to actuator assembly frame 22 by pivot pin 42. One end of toggle link 44 is pivotally connected to lever 40 by pin 46. The other end of toggle link 44 is pivotally connected to slide 50 by pin 48. Slide 50 is mounted for longitudinal reciprocal motion in slots 24 in frame 22 (see also FIG. 4). When lever 40 is pivoted out from the remainder of actuator assembly 20 as shown in FIGS. 2 and 4, slide 50 is in its distal position in slots 24. When lever 40 is pivoted down toward the remainder of actuator assembly 20 as shown in FIG. 3, slide 50 moves proximally in slots 24. In the fully operated position of lever 40, pin 46 has moved slightly past a straight line through pins 42 and 48 so that lever 40 tends to remain in the fully operated position.

The proximal end of a first transversely flexible member 110 is connected to slide 50. Member 110 may be a metal wire or cable, and for convenience herein, member 110 will be referred to as cable 110. Cable 110 passes through the hollow tubular shaft 120 which is the outer member of most of the length of shaft assembly 100. Cable 110 also passes through longitudinal aperture 154 (FIG. 7) in ball 152 and into fastener applying assembly 200. The distal end of cable 110 is connected to anvil part 280 (see also FIG. 5). Accordingly, when lever 40 is pivoted down toward the remainder of actuator assembly 20, cable 110 pulls the lower end of anvil part 280 in toward fastener holding part 210. Cable 110 is transversely flexible so that it does not interfere with the pivoting of joint 150. It should also be noted that cable 110 passes through the point of intersection of axes 102, 104, and 106 (FIG. 1) so that even when placed in tension by operation of lever 40, cable 110 does not tend to alter the relative rotational orientation of assemblies 20 and 200.

Figure 5:
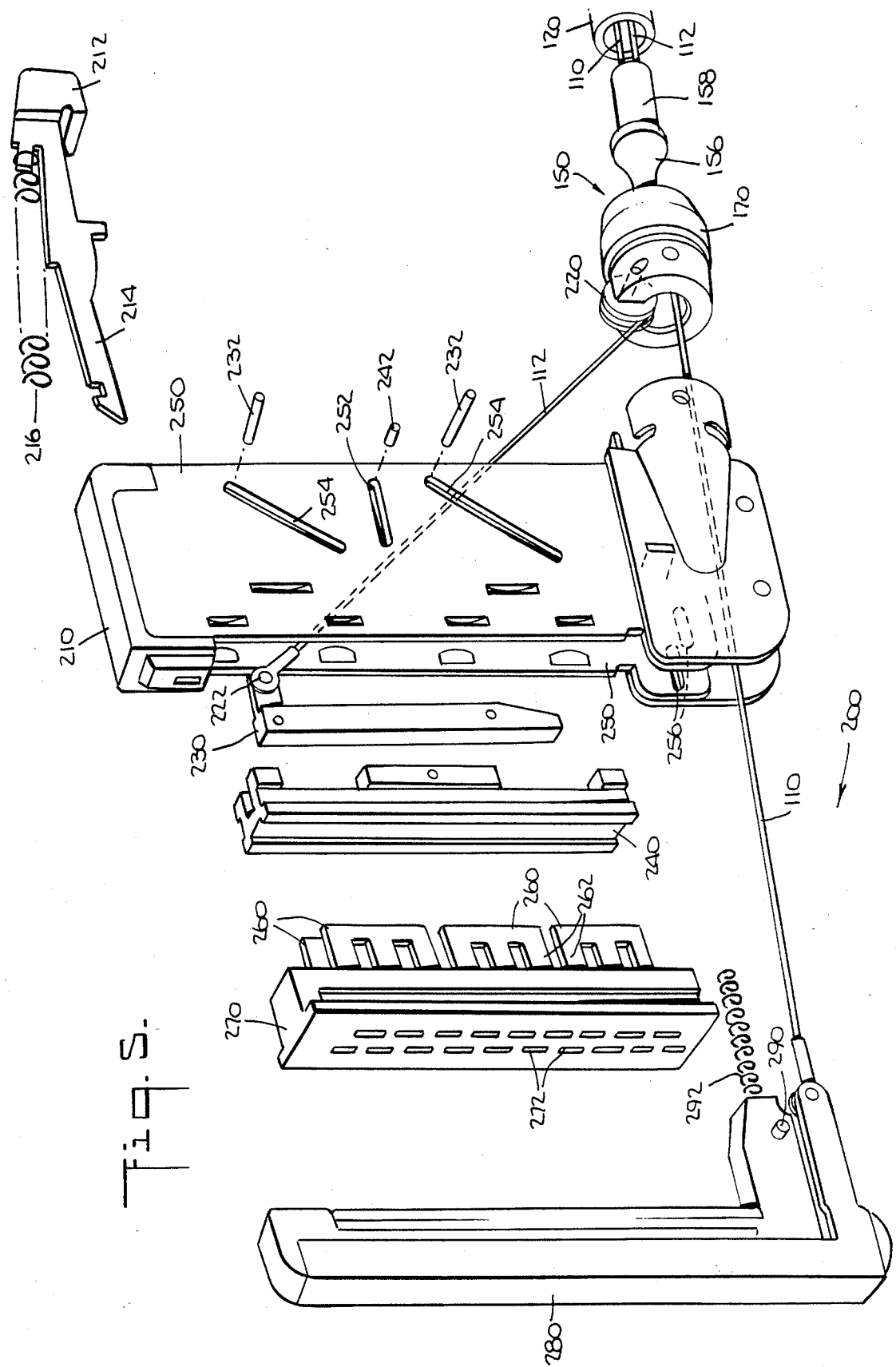
FIGS. 5-7 are exploded perspective views of various portions of the apparatus of FIGS. 1-4.

Returning to FIG. 2, fastener actuator lever 60 is pivotally connected to frame 22 by pin 26. Safety latch 90 is similarly pivotally connected to handle 30 by pin 28. The proximal end of a second transversely flexible member 112 is fixedly attached to frame 22 at anchor 114. Member 112 may be similar to cable 110 and is therefore referred to as cable 112. A proximal portion of cable 112 passes around roller 62 which is rotatably mounted on lever 60 by means of axle 64. After passing roller 62, cable 112 passes distally through shaft 120 and joint 150 and into fastener holding part 210. As is best seen in FIGS. 5 and 8, as cable 112 enters fastener holding part 210, it passes around roller 220. Roller 220 redirects cable 112 up to anchor 222 which connects the distal end of cable 112 to cam bar 230. Accordingly, when lever 60 is pivoted toward handle 30, cable 112 pulls down on cam bar 230. Like cable 110, cable 112 passes through the point of intersection of axes 102, 104, and 106 and is sufficiently transversely flexible so that it does not interfere with the pivoting of joint 150 or tend to alter the relative rotational orientation of assemblies 20 and 200 even when placed in tension by operation of lever 60.

Figure 6:
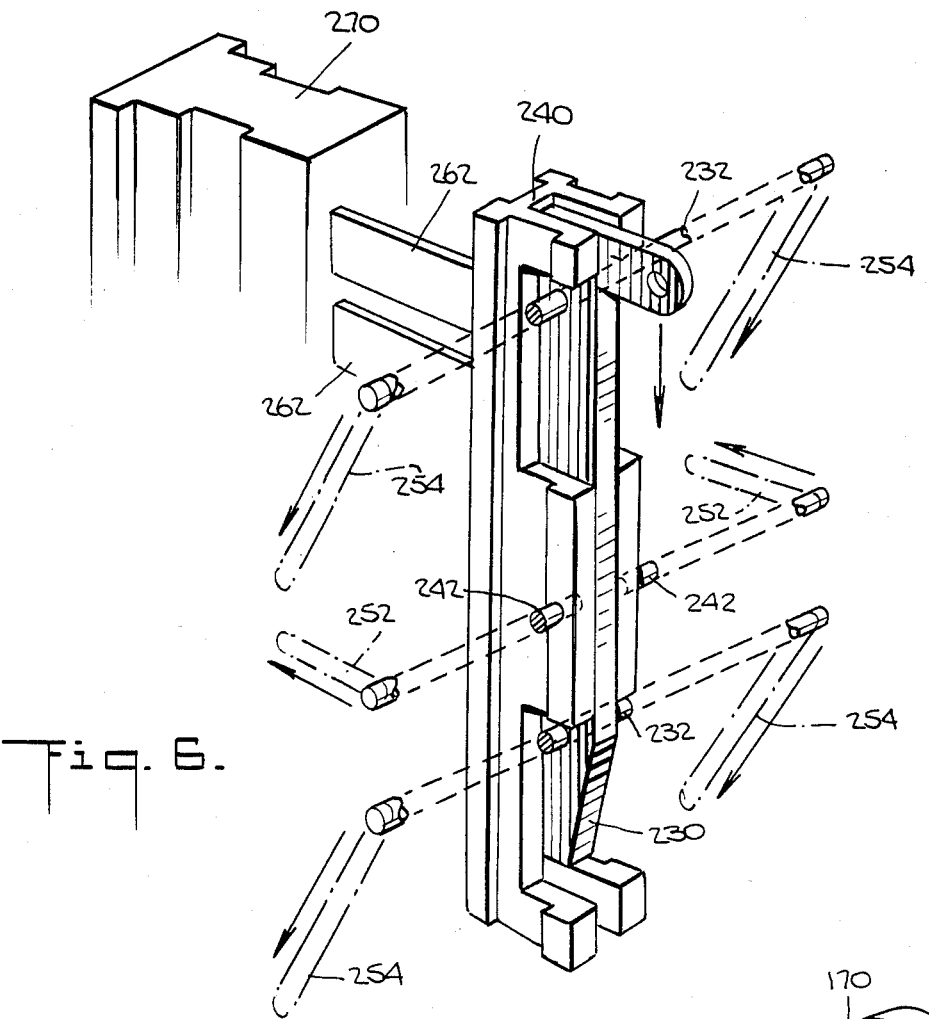

Cam bar 230 is disposed in a proximal-facing channel in pusher actuator member 240 (see FIG. 6). The distal face of cam bar 230 bears on and is slidable along the bottom of this channel in member 240. Pusher actuator member 240 is disposed between two parallel, laterally spaced frame members 250 (FIG. 5) of fastener holding part 210. The distal surface of pusher actuator member 240 bears on the proximal ends of pusher members 260 which have pusher fingers 262 extending into apertures 272 in fastener holder 270 behind staples 202. Pusher actuator member 240 is constrained to move substantially parallel to the axis along which staples 202 are driven by pusher members 260. This constraint is provided by guide pins 242 which extend laterally outward from member 240 into guide slots 252 in frame members 250.

As cam bar 230 is pulled down by cable 112, it is also forced to move in the distal direction by operation of cam follower pins 232 which pass through cam bar 230 and project laterally into cam slots 254 in frame members 250. Cam slots 254 are inclined so that as cam bar 230 moves down in response to the motion of cable 112, it also moves distally. Cam bar 230 slides longitudinally along pusher actuator member 240 so that only the distal motion of cam bar 230 is imparted to member 240. As member 240 moves distally, it drives pusher members 260 and therefore staples 202 in the distal direction. Thus elements 230, 232, 240, 242, 250, 252, 254, and 260 constitute means for converting the downward motion of the distal end of cable 112 into distal motion of staples 202.

The connection between shaft assembly 100 and actuator assembly 20 which permits relative rotation of those assemblies is best seen in FIG. 4. The proximal end of shaft 120 is rotatably mounted in a cylindrical socket 80 formed in the two mirror image halves 70a and 70b of the outer shell of actuator assembly 20. Shell halves 70 are held together by any suitable means such as rivets, adhesive, or the like. Annular collar 122 on shaft 120 is received in annular enlargement 82 of socket 80 to retain shaft 120 in the proper longitudinal position relative to actuator assembly 20. If desired, the amount of rotation of shaft 120 relative to actuator assembly 20 may be limited by cooperating stops 124 on shaft 120 and 84 on actuator assembly shell 70. Shell halves 70 preferably engage shaft 120 with sufficient force to frictionally maintain the relative angular orientation of shaft 120 and actuator assembly 20 established by the user of the apparatus.

Figure 7:
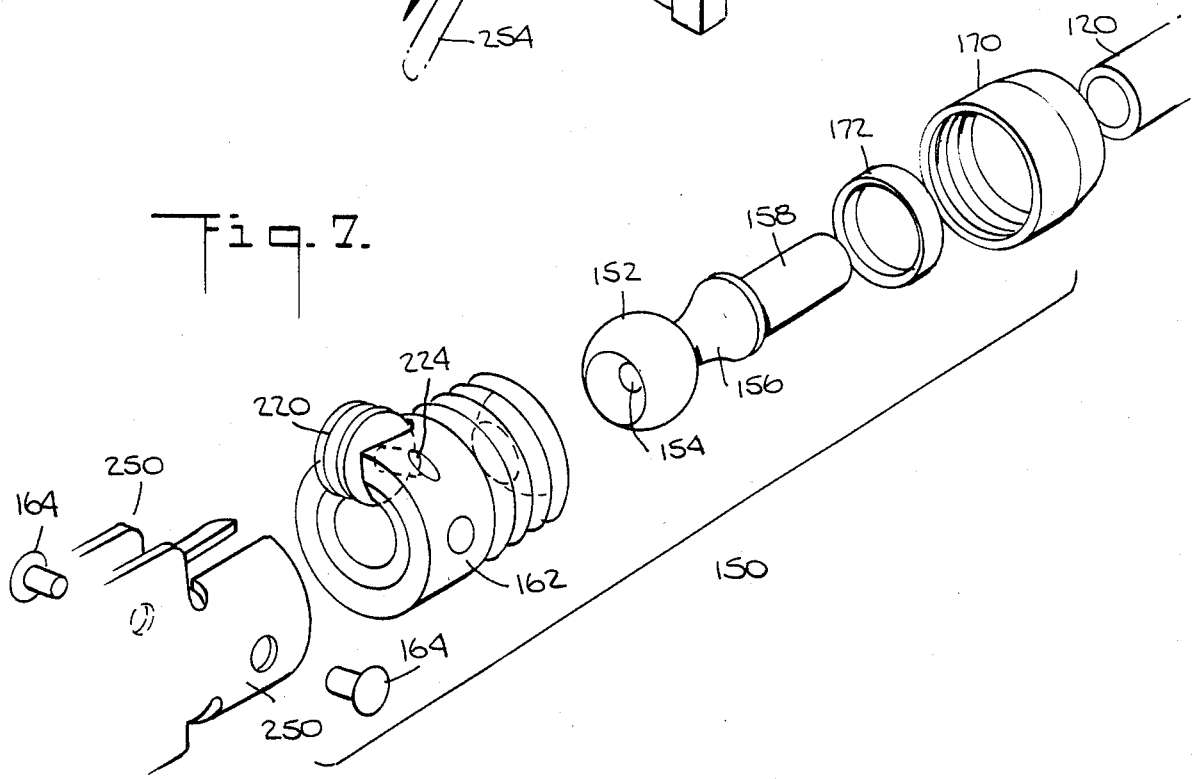

The detailed construction of joint 150 is shown in FIG. 7. Ball 152 is formed at the distal end of hollow, generally frustoconical pedestal 156. A hollow cylindrical shank 158 extends proximally from the base of pedestal 156. Shank 158 is force-fitted into the distal end of shaft 120. Ball 152 fits snugly into socket 160, the construction of which is best seen in FIG. 9. Socket 160 includes distal seat member 162 which carries roller 220 on axle 224 and which is fixedly attached to frame members 250 by pins 164 (FIG. 7). Seat member 162 is hollow and has a proximal-facing annular seat surface 166 for receiving the distal end portion of ball 152. The proximal portion of the cylindrical outer surface of seat member 162 is threaded to receive collar 170. Collar 170 forces an annular retaining ring 172 against a proximal portion of the surface of ball 152. Accordingly, ball 152 is captured between seat surface 166 and retaining ring 172 but can rotate relative to those members about each of axes 102, 104, and 106. Surfaces 166 and 172 preferably engage ball 152 with sufficient force to frictionally maintain whatever relative angular orientation of assemblies 20 and 200 is established by the user of the apparatus. In a particularly preferred embodiment, ball 152 is steel and members 162 and 172 are made of a thermoplastic material such as nylon.

Anvil part 280 is pivotally connected to fastener holding part 210 by means of pin 290 in elongated slots 256 in frame members 250. Slots 256 are elongated parallel to the longitudinal axis of the apparatus so that anvil part 280 can both pivot about pin 290 and translate parallel to slots 256. Anvil part 280 is resiliently biased away from fastener holding part 210 by compression coil spring 292 which is compressed between those parts. Latch 214 is resiliently biased in the proximal direction as shown, for example, in FIG. 8 by compression coil spring 216 acting between latch 214 and the body of fastener holding part 210.

FIG. 13 shows an alternative embodiment in which shaft 120 is longitudinally curved. In other respects, the embodiment shown in FIG. 13 may be identical to the embodiment shown in FIGS. 1–12.

FIG. 14 shows another alternative embodiment in which shaft assembly 100 terminates at approximately the center of fastener applying part 210 rather than at the bottom of that part as in the embodiments of FIGS. 1–13. In this embodiment, additional rollers 226 and 228 are provided in fastener applying part 210 for transferring cable 110 from the longitudinal axis of shaft assembly 100 to the bottom of fastener holding part 210. In all other respects the embodiment of FIG. 14 may be similar to either the embodiment of FIGS. 1–12 or the embodiment of FIG. 13.

We claim:

1. Surgical fastener applying apparatus comprising:
   a distal fastener applying assembly including (a) a fastener holding part initially containing at least one surgical fastener, (b) an anvil part movable relative to the fastener holding part for clamping tissue to be fastened between the fastener holding part and the anvil part, and (c) first means for driving the fastener from the fastener holding part at least partly through the clamped tissue to the anvil part;
   a proximal actuator assembly including second means for producing the work necessasry to operate the first means; and
   a longitudinal shaft assembly for connecting the fastener applying assembly to the actuator assembly, for supporting the fastener applying assembly relative to the actuator assembly, and for operatively transmitting the work produced by the second means to the first means, the shaft assembly including a joint for allowing rotation of the fastener applying assembly relative to the actuator assembly about each of three mutually orthogonal axes.

2. The apparatus defined in claim 1 wherein the three axes intersect one another at a common point.

3. The apparatus defined in claim 2 wherein the joint comprises a ball rotatably mounted in a complementary socket.

4. The apparatus defined in claim 3 wherein the ball and socket frictionally engage one another so that the actuator assembly and fastener applying assembly tend to retain the relative positions into which they are moved.

5. The apparatus defined in claim 1 wherein, except for the joint, the shaft assembly is transversely rigid.

6. The apparatus defined in claim 1 wherein the work produced by the second means is transmitted to the first means by proximal motion of a first member of the shaft assembly.

7. The apparatus defined in claim 6 wherein the portion of the first member longitudinally adjacent the joint is flexible transverse to the longitudinal axis of the shaft assembly.

8. The apparatus defined in claim 7 wherein the portion of the first member longitudinally adjacent the joint is a cable.

9. The apparatus defined in claim 7 wherein the three axes intersect one another at a common point, and wherein the first member passes through the common point.

10. The apparatus defined in claim 9 wherein the joint comprises a ball rotatably mounted in a complementary socket, the center of the ball being coincident with the common point, and the first member passing through apertures in the ball and socket.

11. The apparatus defined in claim 10 wherein the shaft assembly further includes a first tubular shaft section connected between the actuator assembly and one of the ball and socket, and a second tubular shaft section connected between the other of the ball and socket and the fastener applying assembly.

12. The apparatus defined in claim 11 wherein the first member is disposed in the first and second tubular shaft sections for longitudinal motion relative thereto.

13. The apparatus defined in claim 6 wherein the first means drives the fastener in the distal direction and wherein the first means includes third means for converting the proximal motion of the first member to proportional distal motion of the fastener.

14. The apparatus defined in claim 13 wherein the third means comprises:
   a cam and cam follower assembly for converting motion of one of the cam and cam follower transverse to the longitudinal axis of the apparatus to proportional distal motion of the other of the cam and cam follower;
   a longitudinal, transversely flexible second member connected at its proximal end to the distal end of the first member and connected at its distal end to said one of the cam and cam follower; and
   fourth means for redirecting an intermediate portion of the second member from the axis of motion of said one of the cam and cam follower to the axis of motion of the first member.

15. The apparatus defined in claim 1 wherein the actuator assembly further includes fifth means for producing the work necessary to at least partially move the anvil part relative to the fastener holding part to clamp the tissue, and wherein the shaft assembly further includes a third member for operatively transmitting the work produced by the fifth means to the fastener applying assembly to cause the anvil part to move relative to the fastener holding part to clamp the tissue.

16. The apparatus defined in claim 15 wherein the work produced by the fifth means is transmitted to the fastener applying assembly by proximal motion of the third member.

17. The apparatus defined in claim 16 wherein the portion of the third member longitudinally adjacent the joint is flexible transverse to the longitudinal axis of the shaft assembly.

18. The apparatus defined in claim 17 wherein the portion of the third member longitudinally adjacent the joint is a cable.

19. The apparatus defined in claim 17 wherein the three axes intersect one another at a common point, and wherein the third member passes through the common point.

20. The apparatus defined in claim 19 wherein the joint comprises a ball rotatably mounted in a complementary socket, the center of the ball being coincident with the common point, and the third member passing through apertures in the ball and socket.

21. The apparatus defined in claim 20 wherein the shaft assembly further includes a first tubular shaft section connected between the actuator assembly and one of the ball and socket, and a second tubular shaft section connected between the other of the ball and socket and the fastener applying assembly.

22. The apparatus defined in claim 21 wherein the third member is disposed in the first and second tubular shaft sections for longitudinal motion relative thereto.

23. Surgical fastener applying apparatus comprising:

a distal fastener applying assembly including (a) a fastener holding part initially containing at least one surgical fastener, (b) an anvil part movable relative to the fastener holding part for clamping tissue to be fastened between the fastener holding part and the anvil part, and (c) first means for driving the fastener from the fastener holding part at least partly through the clamped tissue to the anvil part;

a proximal actuator assembly including (a) second means for producing at least part of the work required for causing the relative motion of the fastener holding part and the anvil part which clamps the tissue, and (b) third means for producing the work required for operating the first means; and a longitudinal shaft assembly connected between the fastener applying and actuator assemblies and including (a) a longitudinal shaft member including first joint means for allowing rotation of the fastener applying assembly relative to the actuator assembly about each of three mutually orthogonal axes, (b) a first member for operatively transmitting the work produced by the second means to the fastener applying assembly, and (c) a second member for operatively transmitting the work produced by the third means to the first means.

24. The apparatus defined in claim 23 wherein the first and second members move proximally to transmit the associated work, wherein the shaft member is tubular, and wherein each of the first and second members is transversely flexible and disposed in the shaft member for proximal motion relative thereto.

25. The apparatus defined in claim 24 wherein the first means drives the fastener in the distal direction and wherein the first means includes fourth means for converting the proximal motion of the second member to proportional distal motion of the fastener.

26. The apparatus defined in claim 25 wherein the fourth means comprises:

a cam and cam follower assembly for converting motion of one of the cam and cam follower transverse to the longitudinal axis of the apparatus to proportional distal motion of the other of the cam and cam follower;

a longitudinal, transversely flexible third member connected at its proximal end to the distal end of the second member and connected at its distal end to said one of the cam and cam follower; and fifth means for redirecting an intermediate portion of the third member from the axis of motion of said one of the cam and cam follower to the axis of motion of the second member.

27. The apparatus defined in claim 23 wherein the first joint means comprises a ball rotatably mounted in a complementary socket.

28. The apparatus defined in claim 27 wherein the ball and socket frictionally engage one another so that the fastener applying assembly tends to retain its rotational orientation relative to the actuator assembly.

29. The apparatus defined in claim 27 wherein the shaft member is transversely rigid except for the joint means.

30. The apparatus defined in claim 29 wherein the shaft member is longitudinally curved.

31. The apparatus defined in claim 23 wherein the shaft assembly further includes second joint means longitudinally remote from the first joint means for allowing relative rotation of the fastener applying and actuator assemblies about the longitudinal axis of the shaft assembly.

32. The apparatus defined in claim 31 wherein the first and second joint means are respectively adjacent the distal and proximal ends of the shaft assembly.

* * * * *